US010967146B2

(12) United States Patent
Baek et al.

(10) Patent No.: US 10,967,146 B2
(45) Date of Patent: Apr. 6, 2021

(54) CONTROL METHOD AND APPARATUS FOR MANAGING SLEEP ENVIRONMENT

(71) Applicant: SAMSUNG ELECTRONICS CO., LTD., Suwon-si (KR)

(72) Inventors: Dusan Baek, Seoul (KR); Sooyoung Lee, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 275 days.

(21) Appl. No.: 15/744,630

(22) PCT Filed: Jul. 12, 2016

(86) PCT No.: PCT/KR2016/007577
§ 371 (c)(1),
(2) Date: Jan. 12, 2018

(87) PCT Pub. No.: WO2017/010794
PCT Pub. Date: Jan. 19, 2017

(65) Prior Publication Data
US 2018/0207393 A1 Jul. 26, 2018

(30) Foreign Application Priority Data
Jul. 13, 2015 (KR) ........................ 10-2015-0099071

(51) Int. Cl.
A61M 21/02 (2006.01)
H05B 37/02 (2006.01)
(Continued)

(52) U.S. Cl.
CPC ......... A61M 21/02 (2013.01); A61B 5/02055 (2013.01); A61B 5/4809 (2013.01);
(Continued)

(58) Field of Classification Search
CPC ............ A61M 21/02; A61M 2021/005; A61M 2205/3306; A61M 2205/332;
(Continued)

(56) References Cited

U.S. PATENT DOCUMENTS 5,036,858 A * 8/1991 Carter .................. A61B 5/0482
600/27
6,236,622 B1 5/2001 Blackman
(Continued)

FOREIGN PATENT DOCUMENTS

| KR | 10-2012-0051125 A | 5/2012 |
| KR | 10-1460225 B1 | 11/2014 |
| WO | 2015/006364 A2 | 1/2015 |

OTHER PUBLICATIONS

International Search Report, issued by International Searching Authority in corresponding International Application No. PCT/KR2016/007577, dated Oct. 18, 2016, (PCT/ISA/210).
(Continued)

Primary Examiner — Navin Natnithithadha
Assistant Examiner — Sunita Reddy
(74) Attorney, Agent, or Firm — Sughrue Mion, PLLC

(57) ABSTRACT

The present disclosure relates to a technology for a sensor network, machine to machine (M2M), machine type communication (MTC) and internet of things (IoT). The present disclosure can be utilized for intelligent services (smart homes, smart buildings, smart cities, smart cars or connected cars, health care, digital education, retail trading, security and safety-related services, etc.) based on the technology. A control method of a control device for managing a user's sleep environment according to the present invention may comprise the steps of: obtaining sleep-related information of the user on the basis of user sensing data sensed by a sensor; and controlling, on the basis of the sleep-related information, a first wavelength band output of at least one electronic
(Continued)

device comprising a light source. The present invention may also include other embodiments, not limited to the above embodiment.

11 Claims, 11 Drawing Sheets

(51) Int. Cl.
*A61B 5/00* (2006.01)
*A61B 5/0205* (2006.01)
*H05B 47/105* (2020.01)
*A61M 21/00* (2006.01)

(52) U.S. Cl.
CPC .......... *A61B 5/4812* (2013.01); *A61B 5/6898* (2013.01); *H05B 47/105* (2020.01); *A61B 2505/07* (2013.01); *A61M 2021/005* (2013.01); *A61M 2021/0027* (2013.01); *A61M 2021/0044* (2013.01); *A61M 2205/332* (2013.01); *A61M 2205/3303* (2013.01); *A61M 2205/3306* (2013.01); *A61M 2205/3368* (2013.01); *A61M 2205/3375* (2013.01); *A61M 2205/3584* (2013.01); *A61M 2205/50* (2013.01); *A61M 2205/505* (2013.01); *A61M 2205/587* (2013.01); *A61M 2230/06* (2013.01); *A61M 2230/18* (2013.01); *A61M 2230/40* (2013.01); *A61M 2230/42* (2013.01); *A61M 2230/63* (2013.01); *Y02B 20/40* (2013.01)

(58) Field of Classification Search
CPC .. A61M 2205/3368; A61M 2205/3375; A61M 2205/505; A61M 2021/0027; A61M 2205/50; A61M 2230/63; A61M 2230/40; A61M 2230/18; A61M 2230/06; A61M 2205/587; A61M 2205/3584; A61M 2205/3303; A61M 2021/0044; A61M 2230/005; A61M 2230/42; A61B 2505/07; A61B 5/02055; A61B 5/6898; A61B 5/4809; A61B 5/4812; Y02B 20/42; Y02B 20/48; Y02B 20/445; H05B 37/0227
USPC ..................................................... 600/26–28
See application file for complete search history.

(56) References Cited

U.S. PATENT DOCUMENTS

| | | | |
|---|---|---|---|
| 7,280,439 B1 | 10/2007 | Shaddox | |
| 2003/0062856 A1* | 4/2003 | Yano | H05B 39/044 315/291 |
| 2005/0075553 A1* | 4/2005 | Sakai | A61B 5/02438 600/372 |
| 2005/0143617 A1 | 6/2005 | Auphan | |
| 2007/0083079 A1* | 4/2007 | Lee | A61B 5/4806 600/27 |
| 2007/0287930 A1 | 12/2007 | Sutton | |
| 2009/0177327 A1* | 7/2009 | Turner | A47C 21/003 700/275 |
| 2010/0087701 A1 | 4/2010 | Berka et al. | |
| 2010/0331606 A1* | 12/2010 | Wong | A61M 21/02 600/27 |
| 2011/0010014 A1* | 1/2011 | Oexman | A47C 27/061 700/276 |
| 2011/0215725 A1* | 9/2011 | Paolini | G01J 3/2803 315/153 |
| 2011/0295083 A1* | 12/2011 | Doelling | A61B 5/103 600/301 |
| 2013/0234823 A1* | 9/2013 | Kahn | A61B 5/681 340/3.1 |
| 2014/0265480 A1* | 9/2014 | Perrin | B60N 2/26 297/217.4 |
| 2014/0334653 A1* | 11/2014 | Luna | H05B 47/105 381/332 |
| 2015/0238137 A1* | 8/2015 | Eyal | A61B 5/4815 600/508 |
| 2016/0015315 A1* | 1/2016 | Auphan | A61B 5/4815 600/301 |
| 2016/0151603 A1 | 6/2016 | Shouldice et al. | |

OTHER PUBLICATIONS

Written Opinion, issued by International Searching Authority in corresponding International Application No. PCT/KR2016/007577, dated Oct. 18, 2016, (PCT/ISA/237).

* cited by examiner

CONTROL METHOD AND APPARATUS FOR MANAGING SLEEP ENVIRONMENT

TECHNICAL FIELD

The present invention relates to a method and apparatus for controlling an electronic device including a light source in order to manage a user sleep environment.

BACKGROUND ART

Internet has been innovated from a human-based connection network in which a human generates and consumes information to an Internet of Things (IoT) network that gives, receives and processes information to and from distributed constituent elements such as things. Internet of Everything (IoE) technology has appeared in which big data processing technology is combined with IoT technology through connection to a cloud server. In order to implement the IoT, technology elements such as sensing technology, wired and wireless communication and network infrastructure, service interface technology, and security technology are required; thus, nowadays, research is being carried out on technology of a sensor network, Machine to Machine (M2M) communication, and Machine Type Communication (MTC) for connection between things.

In an IoT environment, an intelligent Internet technology service that collects and analyzes data generated in connected things to provide a new value to a human life may be provided. The IoT may be applied to the field of a smart home, smart building, smart city, smart car or connected car, smart grid, health care, smart home appliances, and high-tech medical service through fusion and complex connections between existing information technology (IT) and various industries.

For example, a smart home means a home environment in which devices including home appliances connected to a home network can be controlled almost regardless of time and location. Nowadays, in order to implement a smart home, various smart home devices have been developed, and related standardization work is being performed in various fields such as a home platform, wired and wireless home networking, intelligent information home appliances, and a green home.

In a smart home environment, various electronic devices such as a home appliance device and a user terminal may be registered at a control device (e.g., application processor (AP), and the registered electronic device and the control device may perform communication by wire or wireless.

Nowadays, in a smart home field, various home services that can provide convenience to a user are developing. For example, an entire sleep environment from when a user prepares for sleep until after wake-up may be adaptively applied to the user.

DISCLOSURE OF INVENTION

Technical Problem

The present invention has been made in view of the above problem and provides a method of controlling a sleep environment for an entire sleep process from when a user prepares for sleep until the user reaches a normal state after wake-up in order to provide a more effective and convenient sleep environment to a user in a smart home environment.

The present invention has been made in view of the above problem and further provides a method of controlling brightness and a wavelength of an electronic device including a light source in order to mitigate a user visual stimulus in a sleep process in order to control a sleep environment.

Solution to Problem

In accordance with an aspect of the present invention, a method of controlling a control device for managing a user sleep environment includes obtaining user sleep related information based on user sensing data sensed by a sensor and adjusting a first wavelength band output of at least one electronic device including a light source based on the sleep related information.

In accordance with another aspect of the present invention, a control device for managing a user sleep environment includes a controller configured to obtain user sleep related information based on user sensing data sensed by a sensor and to generate a control signal that adjusts a first wavelength band output of at least one electronic device including a light source based on the sleep related information; and a transceiver configured to transmit the control signal to the at least one electronic device.

Advantageous Effects of Invention

According to an exemplary embodiment of the present invention, by detecting various sleep related information in a user in a hypnagogic stage and by applying a system to a user instead of applying a user to a system, a smart home environment can be provided in which finer control is available.

For the fine control for managing a user sleep environment according to an exemplary embodiment of the present invention, elements of brightness and a color (wavelength) of light of an electronic device including a light source can be adaptively controlled to a user at each of before sleep, during sleep, and after wake-up.

MODE FOR THE INVENTION

Figure 1:
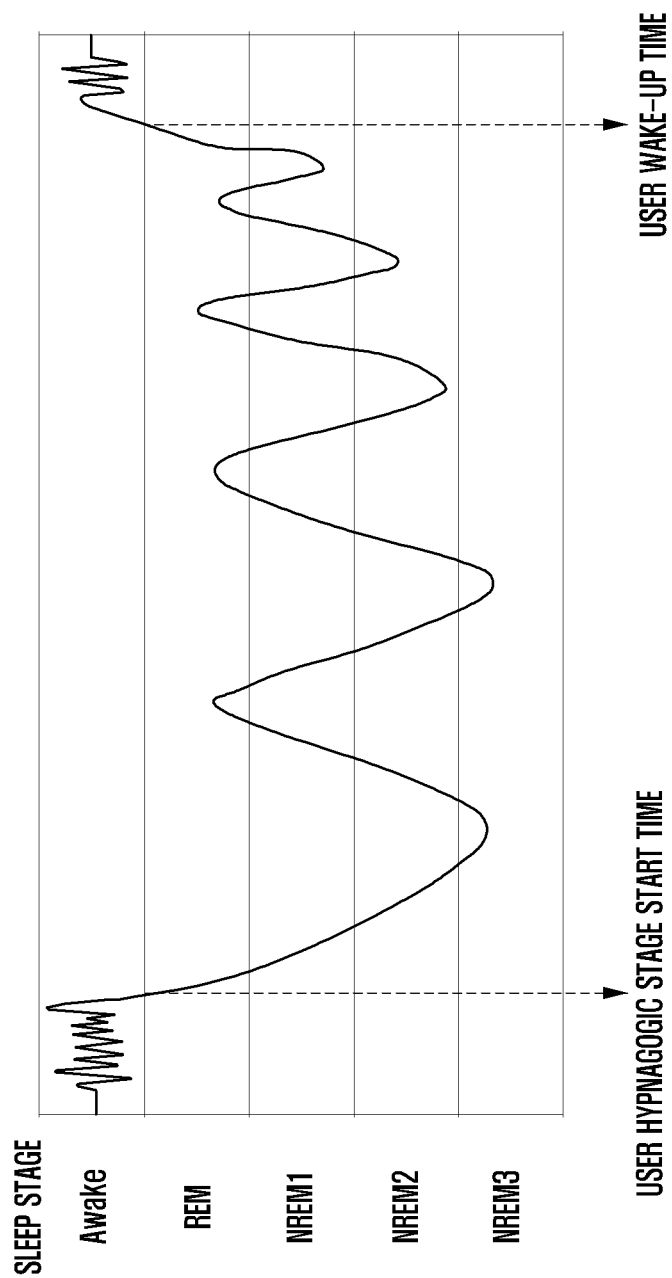
FIG. 1 is a graph illustrating a user sleep stage.

Hereinafter, exemplary embodiments of the present disclosure are described in detail with reference to the accompanying drawings. While the present disclosure may be embodied in many different forms, specific embodiments of the present disclosure are shown in the drawings and are described herein in detail with the understanding that the present disclosure is to be considered as an exemplification of the principles of the invention and is not intended to limit the invention to the specific embodiments illustrated. The same reference numbers are used throughout the drawings to refer to the same or like parts.

An expression "comprising" or "may comprise" used in the present disclosure indicates presence of a corresponding function, operation, or element and does not limit an additional at least one function, operation, or element. Further, in the present disclosure, a term "comprise" or "have" indicates presence of a characteristic, numeral, step, operation, element, component, or combination thereof described in a specification and does not exclude presence or addition of at least one other characteristic, numeral, step, operation, element, component, or combination thereof.

In the present disclosure, an expression "or" includes any combination or all combinations of together listed words. For example, "A or B" may include A, B, or A and B.

An expression of "first", "second", "primary", and "secondary" in the present disclosure may represent various elements of the present disclosure, but such an expression does not limit the corresponding elements. For example, the expressions do not limit order and/or importance of the corresponding elements. The expressions may be used for distinguishing one element from another element. For example, both a first user device and a second user device are user devices and represent different user devices. For example, a first element may be referred to as a second element without deviating from the scope of the present disclosure and, similarly, a second element may be referred to as a first element.

When it is described that an element is "connected" or "electrically connected" to another element, the element may be "directly connected" or "directly electrically connected" to the other element or may be "connected" or "electrically connected" to the other element through a third element. However, when it is described that an element is "directly connected" or "directly electrically connected" to another element, no element may exist between the element and the other element.

Terms used in the present application are used for describing a specific exemplary embodiment and do not limit the present disclosure. Unless the context otherwise clearly indicates, words used in the singular include the plural, the plural includes the singular.

Unless differently defined, entire terms used here including a technical or scientific term have the same meaning as a meaning that may be generally understood by a person of common skill in the art. It should be understood that terms defined in a general dictionary use have a meaning corresponding with that of a context of related technology and are not to be understood as an ideal or excessively formal meaning unless explicitly defined.

An electronic device according to an exemplary embodiment of the present disclosure may include at least one of a smart phone, a tablet Personal Computer (PC), a mobile phone, a video phone, an e-book reader, a desktop PC, a laptop PC, a netbook computer, a Personal Digital Assistant (PDA), a Portable Multimedia Player (PMP), an MPEG 3 (MP3) player, a mobile medical equipment, a camera, or a wearable device (e.g., Head-Mounted-Device (HMD) such as electronic glasses), electronic clothing, an electronic bracelet, an electronic necklace, electronic accessory, an electronic tattoo, and a smart watch.

According to an exemplary embodiment, the electronic device may be a smart home appliance. For the smart home appliance, for example, the electronic device may include at least one of a television, a Digital Video Disk (DVD) player, an audio device, a refrigerator, an air conditioner, a vacuum cleaner, an oven, a microwave oven, a washing machine, an air cleaner, a set-top box, a television box (e.g., Samsung HomeSync™, AppleTV™, or Google TV™), game consoles, an electronic dictionary, an electronic key, a camcorder, and an electronic frame.

According to an exemplary embodiment, the electronic device may include at least one of various medical equipment (e.g., a Magnetic Resonance Angiography (MRA) device, a Magnetic Resonance Imaging (MRI) device, a Computed Tomography (CT) device, a scanning device, and an ultrasonic wave device), a navigation device, a Global Positioning System (GPS) receiver, an Event Data Recorder (EDR), a Flight Data Recorder (FDR), a vehicle infotainment device, an electronic equipment for ship (e.g., navigation device and gyro compass for ship), avionics, a security device, a head unit for a vehicle, an industrial or home robot, an automated teller machine of a financial institution, and a point of sales (POS) of a store.

According to an exemplary embodiment, the electronic device may include at least one of a portion of furniture or a building/structure, an electronic board, an electronic signature receiving device, a projector, and various measurement devices (e.g., water supply, electricity, gas, or electric wave measurement device). The electronic device according to an exemplary embodiment of the present disclosure may be at least one combination of the foregoing various devices. Further, the electronic device according to an exemplary embodiment of the present disclosure may be a flexible device. Further, the electronic device according to an exemplary embodiment of the present disclosure is not limited to the foregoing devices.

Hereinafter an electronic device according to various exemplary embodiments of the present disclosure will be described with reference to the accompanying drawings. A term of a user used in various exemplary embodiments may indicate a person using an electronic device or a device (e.g., artificial intelligence electronic device) using the electronic device.

In this specification, "user sleep environment management" may indicate that a control device (e.g., application processor (AP)) controls, for example, a visual output of an electronic device registered at the same based on sensing data obtained in a user sleep process in a smart home system.

In this specification, a "user sleep process" may include an entire process from when a user prepares for sleep until reaching a normal state after wake-up.

FIG. 1 is a graph illustrating a user sleep stage.

As shown in FIG. 1, a user sleep related state may include an awake stage, a rapid-eye movement (REM) sleep stage, and a non-rapid-eye movement (NREM 1-3) sleep stage. When a user sleeps, a time that passes from an awake stage to a sleep stage may be regarded as a user hypnagogic stage or time. When the user is in a NREM sleep stage, the user may be regarded as having fallen into a relatively deep sleep. While the user sleeps, a time in which the user passes from a REM sleep stage to an awake stage may be regarded as a user wake-up time.

Figure 2A:
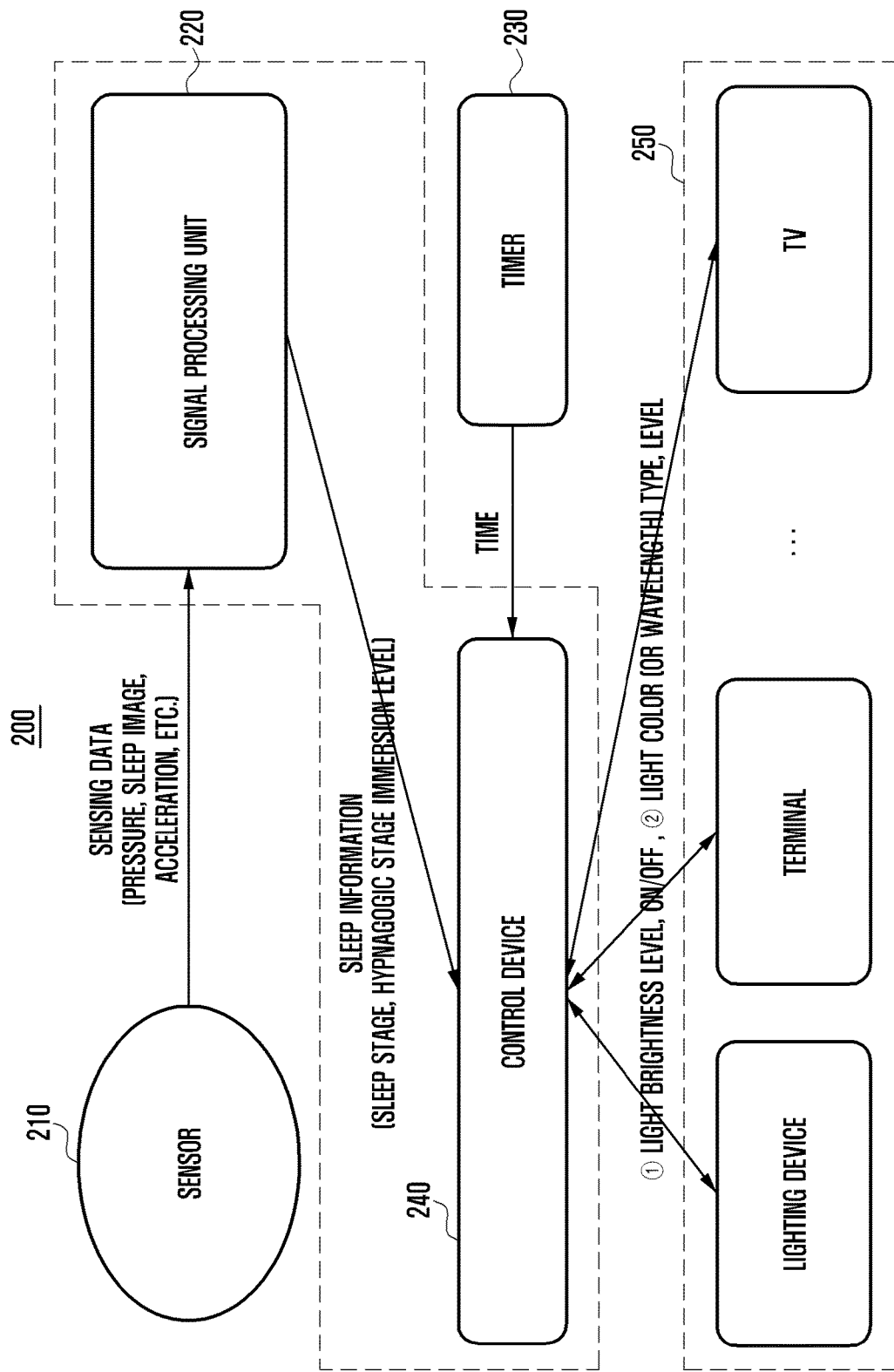
FIG. 2A is a diagram illustrating a smart home system according to an exemplary embodiment of the present invention.

FIG. 2A is a diagram illustrating a smart home system 200 for managing a user sleep environment according to an exemplary embodiment of the present disclosure.

With reference to FIG. 2A, a smart home system 200 for managing a user sleep environment may include a sensor 210, a signal processing unit 220, timer 230, a control device 240, and at least one electronic device 250. Two or more constituent elements may be implemented into one device. For example, the signal processing unit 220 and the sensor 210 may form one device or the signal processing unit 220 and the control device 240 may form one device. Each constituent element may give and receive a signal through wire or wireless communication.

The sensor 210 may sense a user state to generate sensing data. In order to manage a user sleep environment, sensing data generated by the sensor 210 may include information of at least one of, for example, a pressure, an image, a vibration, and acceleration. The sensor 210 may include, for example, a gesture sensor, gyro sensor, atmospheric pressure sensor, acceleration sensor, grip sensor, proximity sensor, red-green-blue (RGB) sensor, bio-sensor, temperature/humidity sensor, illumination sensor, and ultraviolet (UV) sensor.

The signal processing unit 220 may process the sensing data to generate sleep information. The sleep information may be referred to as sleep data, sleep related data, or sleep related information. The signal processing unit 220 may process the sensing data to obtain data of at least one of breath, movement, heart rate variability, or heart rate. In this case, a data pattern may be stored at a database, and the signal processing unit 220 may obtain the meaningful data (breath, movement, heart rate variability, or heart rate) from the sensing data based on the data pattern.

The signal processing unit 220 may calculate at least one of a data change, a data stabilizing speed, and a data value range of the obtained data to generate the sleep information. The sleep information may include, for example, a user sleep stage or a hypnagogic stage immersion level. The user hypnagogic stage immersion level represents an immersion execution rate until the user enters a NREM stage, when the user sleeps. The signal processing unit 220 may compare at least one of a data change, a data stabilizing speed, or a data value range of the obtained data with a close reference value in data stored at a database to calculate the user sleep stage and/or hypnagogic stage immersion level. The signal processing unit 220 may accumulate again the calculated user sleep stage and/or hypnagogic stage immersion level at the database to store a statistic value.

The timer 230 may provide time information to the control device 240.

The control device 240 may generate a control signal that controls at least one electronic device 250 based on the sleep information.

The at least one electronic device 250 may include a lighting device including a light source and an electronic device (e.g., terminal, television) including a display. For example, the at least one electronic device 250 may be previously registered at the control device 240.

The control device 240 may control an output through a light source of the at least one electronic device 250 based on the sleep information. For example, the control device 240 may entirely control at least one electronic device 250 and may individually control at least one electronic device 250 according to a characteristic of each electronic device 250.

In order to obtain the sleep information, when the control device 240 is an element divided from the signal processing unit 220, the control device 240 may receive the sleep information generated in the signal processing unit 220, and when the control device 240 is an element including the signal processing unit 220, the control device 240 may generate the sleep information based on the sensing data.

Figure 2B:
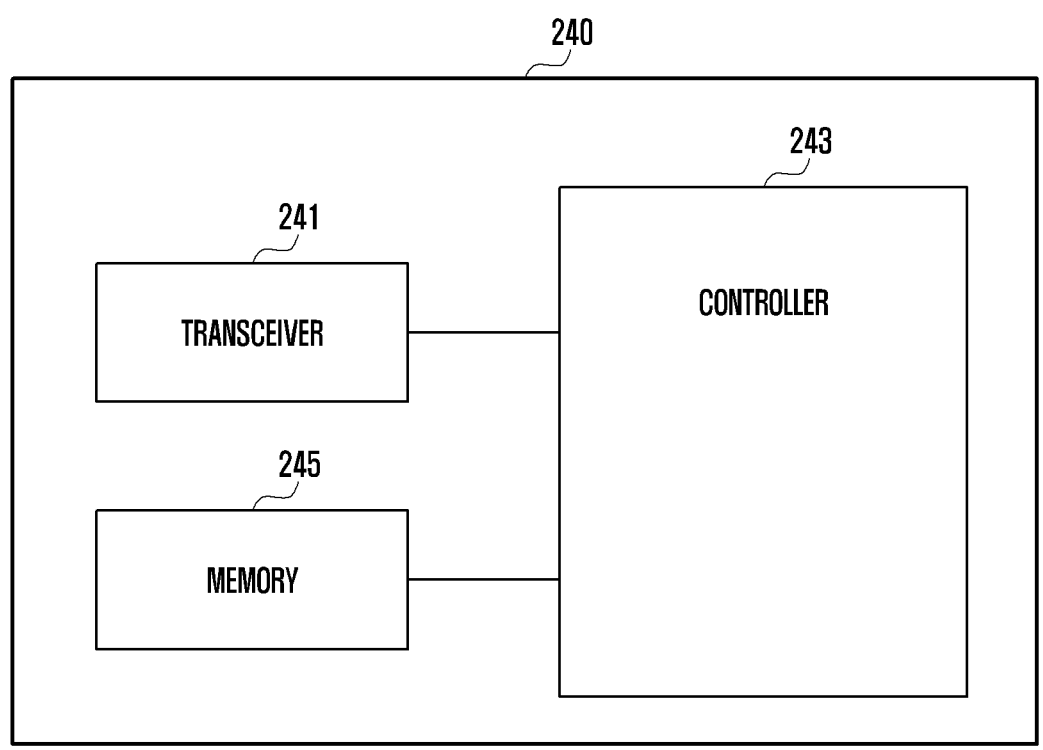
FIG. 2B is a block diagram illustrating a configuration of a smart home control device according to an exemplary embodiment of the present invention.

With reference to FIG. 2B, the control device 240 may include a transceiver 241, controller 243, and memory 245.

The transceiver 241 may give and receive a signal to and from another apparatus. For example, the transceiver 241 may transmit a control signal for controlling the at least one electronic device 250 to the at least one electronic device 250. The transceiver 241 may receive the sleep information from the signal processing unit 220. When the controller 243 performs a function of the signal processing unit 220, the transceiver 241 may receive sensing data from the sensor 210.

The controller 243 may control general operations of the control device 240. The controller 243 may control an output through a light source of the at least one electronic device 250 based on the obtained sleep information. The controller 243 may include a function of the signal processing unit 220.

The controller 243 may control, for example, brightness (level or on/off) of light of the at least one electronic device 250 based on the sleep information and control an output of a wavelength band (color of light, a kind or a level of a wavelength) of light of the at least one electronic device 250.

The memory 245 may store a database including data related to the sleep information. The database may store, for example, information of the control signal corresponding to the user sleep stage and/or hypnagogic stage immersion level and store a statistic value of accumulated data.

Figure 3:
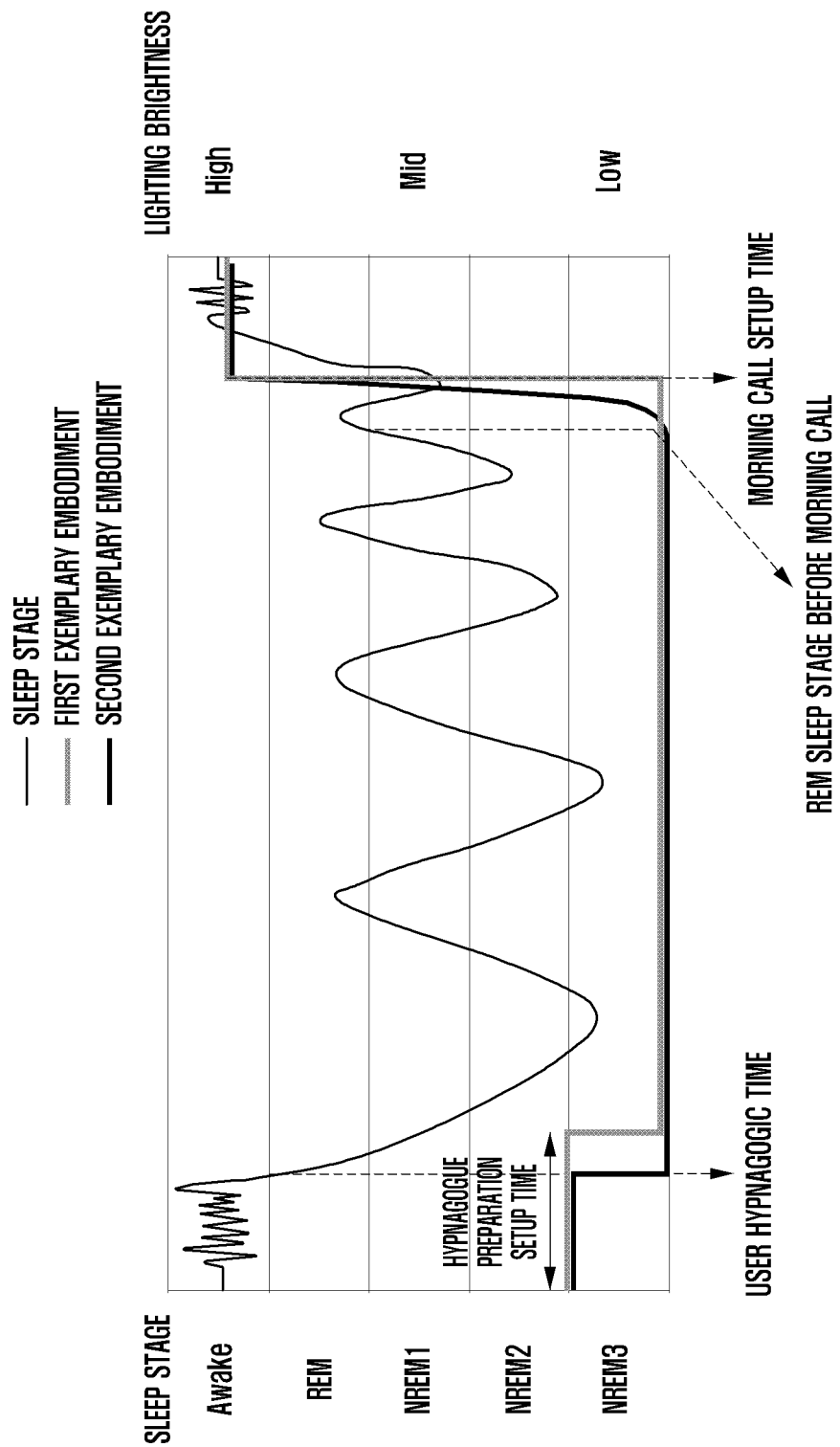
FIG. 3 is a graph illustrating a control method of managing a user sleep environment in a smart home system according to first and second exemplary embodiments of the present invention.

FIG. 3 is a graph illustrating a control method of a control device 240 for managing a user sleep environment in a smart home system 200 according to first and second exemplary embodiments of the present disclosure.

According to a first exemplary embodiment of the present disclosure, when the user prepares for sleep, the control device 240 may obtain hypnagogic stage preparation information through the sensor 210 or may obtain hypnagogic stage preparation information by a user input. The control device 240 may maintain brightness of at least one electronic device 250 to a predetermined relatively low value for a predetermined hypnagogic stage preparation setup time after the user hypnagogic stage preparation is determined and may turn off the at least one electronic device 250 or lighting and/or display of the at least one electronic device 250 after the hypnagogic stage preparation setup time has elapsed.

Thereafter, when a predetermined morning call setup time has arrived, the control device 240 may turn on the at least one electronic device 250 and control a brightness thereof to a predetermined relatively high value.

That is, according to the first exemplary embodiment, the control device 240 may manage a user sleep environment according to a setup regardless of a user state in sleep.

According to a second exemplary embodiment of the present disclosure, when the user performs a hypnagogic stage preparation, the control device 240 may obtain hypnagogic stage preparation information through the sensor 210 or may obtain hypnagogic stage preparation information by a user input. After the user hypnagogic stage preparation is determined, the control device 240 may maintain brightness of at least one electronic device 250 to a predetermined relatively low value. The control device 240 may obtain a user sleep related state from sensing data in which the sensor 210 senses and generates a user state. For example, after the user hypnagogic stage preparation is determined, when the user is in a hypnagogic stage, the control device 240 may turn off the at least one electronic device 250 controlled to brightness of the predetermined relatively low value or lighting and/or display of the at least one electronic device 250. This is because it is determined that the user is in a sleep state.

Thereafter, when a user REM sleep stage comes immediately before a predetermined morning call setup time, the electronic device 250 may turn on the at least one electronic device 250 and slowly increase brightness thereof. At the morning call setup time, the electronic device 250 may control brightness of the at least one electronic device 250 to a predetermined relatively high value.

That is, according to a second exemplary embodiment, sleep environment management adaptive to a user is available using a user sleep related state obtained based on user state sensing data.

Figure 4:
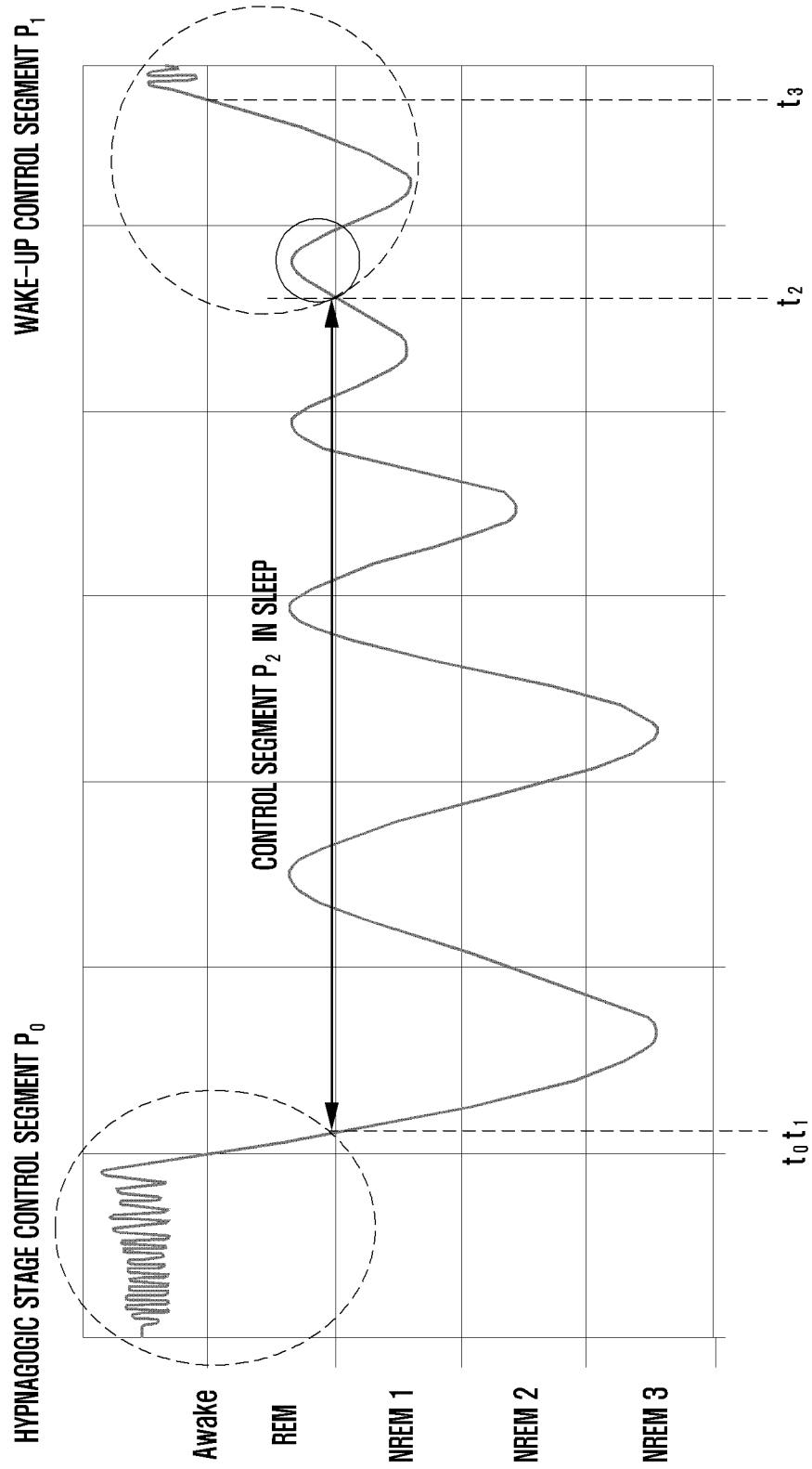
FIG. 4 is a graph illustrating a control method of managing a user sleep environment in a smart home system according to a third exemplary embodiment of the present invention.

FIG. 4 is a graph illustrating a control method of managing a user sleep environment in a smart home system 200 according to a third exemplary embodiment of the present disclosure.

According to a third exemplary embodiment, the control device 240 may manage a user sleep environment appropriate to each segment at each of a hypnagogic stage control segment $P_0$, a wake-up control segment $P_1$, and a control segment $P_2$ in sleep.

The hypnagogic stage control segment $P_0$ may include a time segment $t_1$ until the user enters a first NREM sleep stage after user hypnagogic stage preparation is determined and after a hypnagogic stage start time $t0$ has elapsed. A control method of a system at the hypnagogic stage control segment $P_0$ will be described with reference to FIG. 5A.

The wake-up control segment $P_1$ may include a time segment from a time $t2$ in which the user enters a REM sleep stage immediately before wake-up until a predetermined time has elapsed after a time $t3$ in which the user awakes. A control method of a system at the wake-up control segment $P_1$ will be described with reference to FIG. 5B.

The control segment $P_2$ in sleep may include a time segment between the hypnagogic stage control segment $P_0$ and the wake-up control segment $P_1$. A control method of a system at the control segment $P_2$ in sleep will be described with reference to FIG. 5C.

Figure 5A:
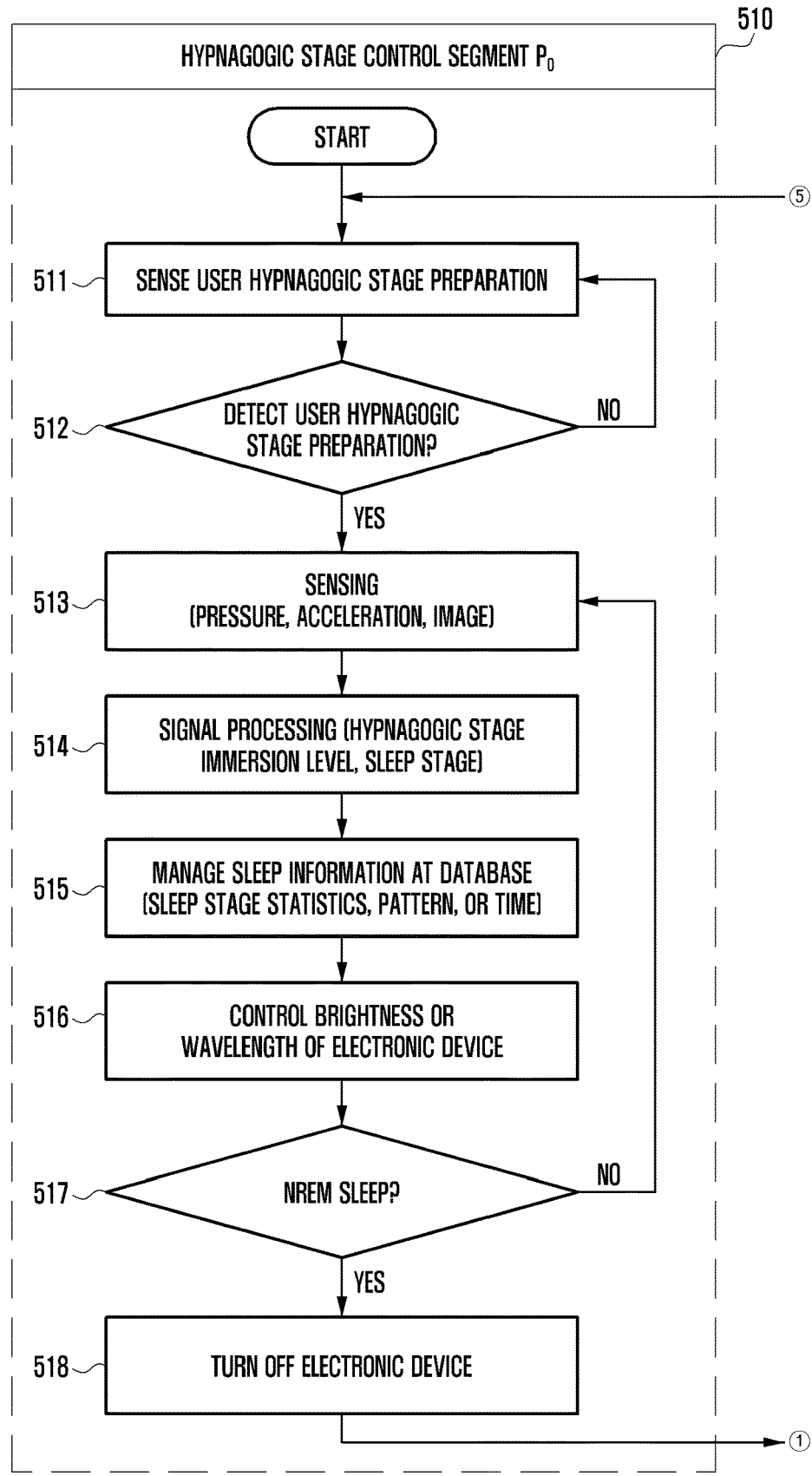
FIG. 5A is a flowchart illustrating a control method at a hypnagogic stage control segment according to a third exemplary embodiment of the present invention.

FIG. 5A is a flowchart illustrating a control method 510 of a smart home system 200 at the hypnagogic stage control segment $P_0$.

The sensor 210 may sense a user state at step 511. For example, the sensor 210 may be activated at a predetermined time or may be activated at a moment of detecting user existence. In order to obtain information related to whether there is initial user hypnagogic stage preparation, the sensor 210 may sense a user state that can determine user hypnagogic stage preparation. For example, the sensor 210 may obtain a user image (e.g., an image of an in-bed state). However, the present disclosure is not limited thereto.

The signal processing unit 220 may detect the user hypnagogic stage preparation based on sensing data of the sensor 210 at step 512. The sensor 210 may sense a user state at step 513. The sensor 210 may receive a signal in which the user hypnagogic stage preparation has been detected from the signal processing unit 220 and perform sensing of step 513 or may perform sensing of a user state regardless of this. The sensor 210 may generate sensing data through sensing of at least one of a pressure, an image, a vibration, and acceleration.

Figure 6:
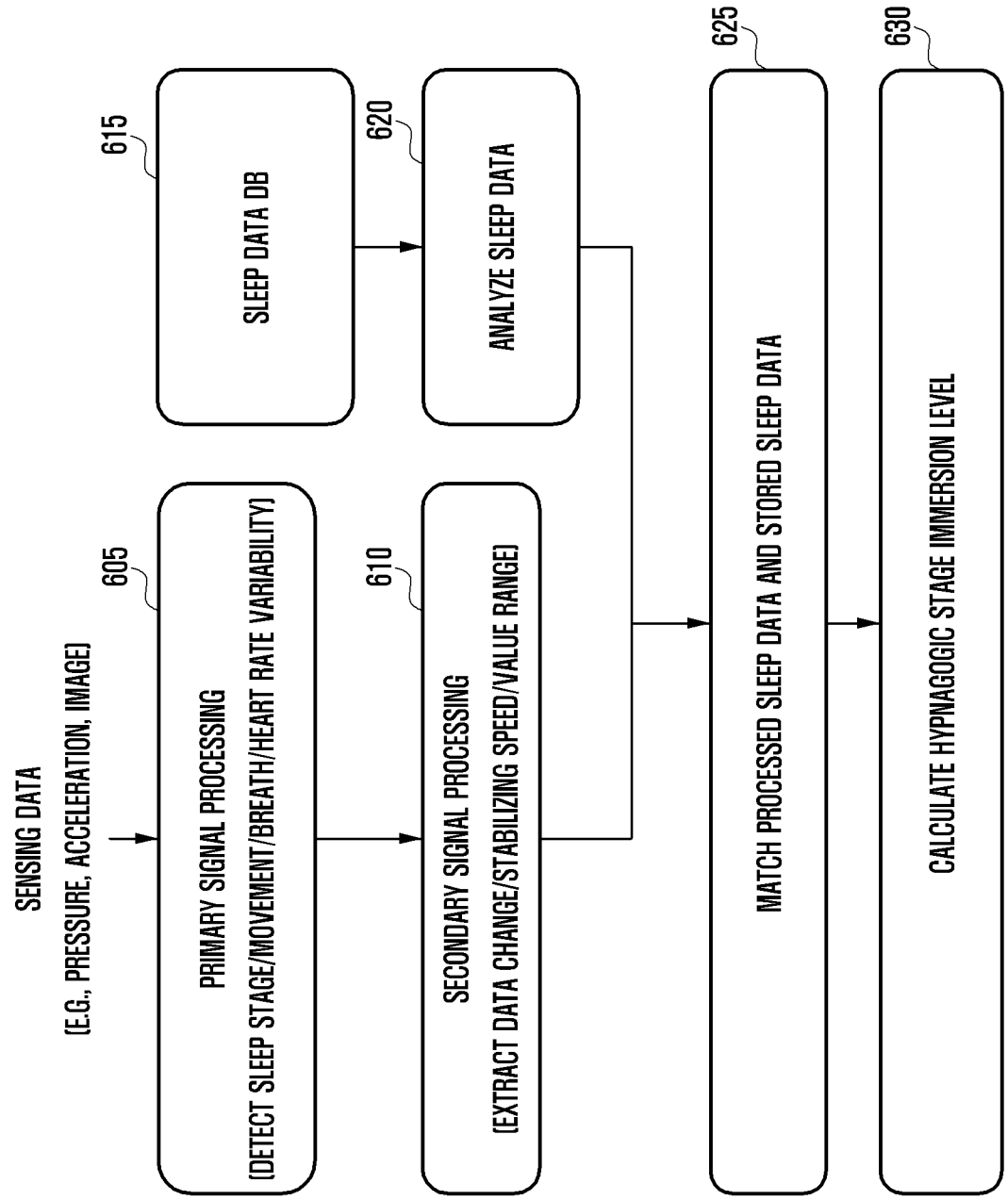
FIG. 6 is a diagram illustrating a method of calculating sleep information with sensing data according to a third exemplary embodiment of the present invention.

The signal processing unit 220 may perform a signal processing of the sensing data to calculate user sleep information, for example, a user sleep stage and/or hypnagogic stage immersion level at a corresponding time point at step 514. FIG. 6 illustrates an example in which the signal processing unit 220 processes the sensing data to obtain user sleep information.

The signal processing unit 220 may accumulate obtained sleep information and sleep data at a database and manage the database at step 515. The database may be updated and stored based on accumulated data of statistics, pattern, or time information of sleep data at each sleep step.

The control device 240 may control brightness or a wavelength (light color) of at least one electronic device 250 at step 516 based on the sleep information. For example, when user hypnagogic stage preparation is detected, the control device 240 reduces brightness of the at least one electronic device 250 step-by-step from a maximum brightness (e.g., 10 lux) or less based on a user hypnagogic stage immersion level.

Figure 8:
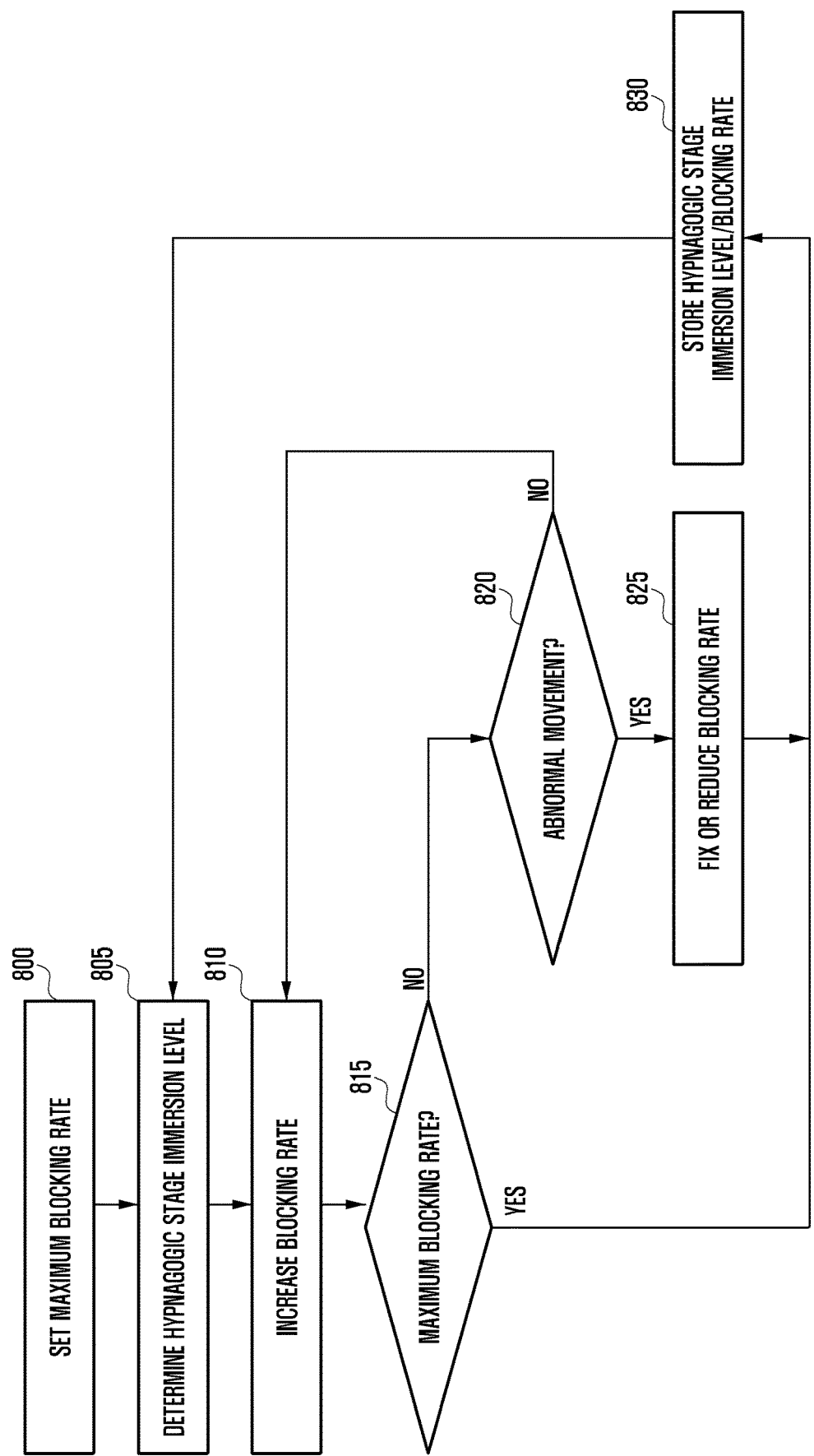
FIG. 8 is a flowchart illustrating a method of controlling a blocking rate of a first wavelength band output of an electronic device for managing a user sleep environment according to a third exemplary embodiment of the present invention.

Further, when user hypnagogic stage preparation is detected, the control device 240 may adjust a first wavelength band output of the at least one electronic device 250 based on a user hypnagogic stage immersion level. For example, the control device 240 may increase a blocking ratio of the first wavelength band output step-by-step within a maximum blocking ratio based on a user hypnagogic stage immersion level. The first wavelength band may include, for example, a wavelength (hereinafter, blue wavelength) that emits blue light. The blue wavelength may be a short wavelength, for example, a wavelength based on 380 nm-500 nm or 460 nm. FIG. 8 illustrates an example in which the control device 240 controls a blocking ratio of the first wavelength band output.

The control device 240 may detect whether the user enters a first NREM sleep stage at step 517. Accordingly, the control device 240 may turn off the at least one electronic device 250 or may turn off lighting and/or display of the at least one electronic device 250 at step 518.

Figure 5B:
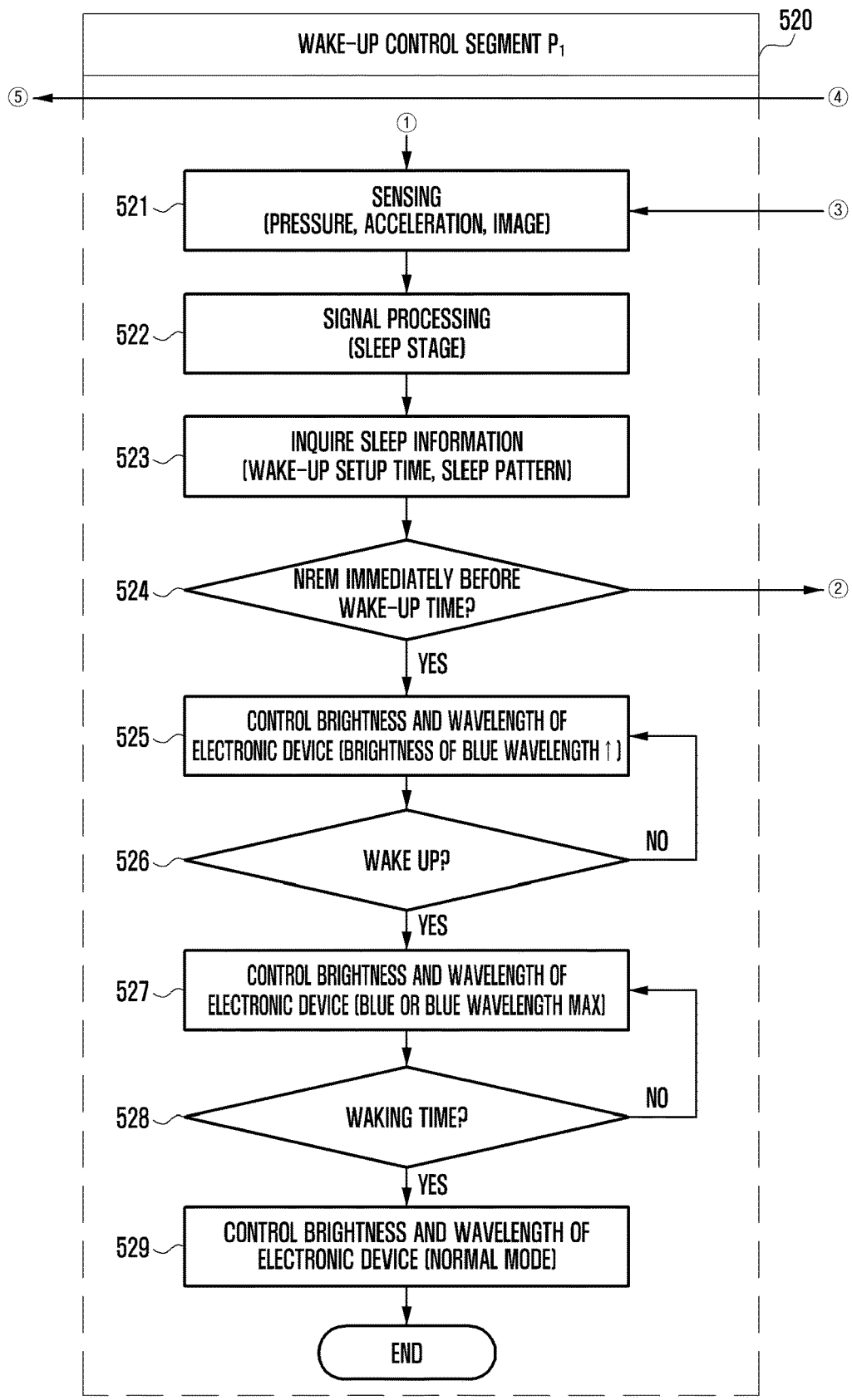
FIG. 5B is a flowchart illustrating a control method at a wake-up control segment according to a third exemplary embodiment of the present invention.

FIG. 5B is a flowchart illustrating a control method 520 of a smart home system 200 at the wake-up control segment $P_1$.

The sensor 210 may sense a user sleep state at step 521. The sensor 210 may generate sensing data through sensing of at least one of a pressure, an image, a vibration, and acceleration.

The signal processing unit 220 may perform a signal processing of sensing data of the sensor 210 to determine a user sleep stage at step 522.

The control device 240 may inquire sleep data (e.g., a predetermined wake-up time and/or a user sleep pattern) stored at the database at step 523.

The control device 240 may determine at step 524 whether the user enters a NREM sleep stage immediately before wake-up based on the inquired sleep data. For example, when a wake-up time is preset, the control device 240 may determine whether the user enters a predetermined NREM sleep stage immediately before a wake-up time. If a wake-up time is not preset or is set based on a substantial user wake-up time, the control device 240 may match user sleep stage information obtained from the signal processing unit 220 to a user sleep pattern obtained from the database to determine whether the user enters an estimated NREM sleep stage immediately before a wake-up time.

If the user enters a NREM sleep stage immediately before a wake-up time, the control device 240 at step 525 may control brightness and/or a wavelength of at least one electronic device 250. For example, the control device 240 may increase brightness step-by-step of at least one electronic device 250. When a first wavelength band output is partially blocked at the foregoing control segment (e.g., a hypnagogic stage control segment $P_0$), the control device 240 may reduce a blocking ratio of the first wavelength band output. The first wavelength band may include, for example, a blue wavelength.

The control device 240 may detect at step 526 whether the user wakes up based on a user sleep stage.

If user wake-up is detected, the control device 240 may control brightness and/or a wavelength of at least one electronic device 250 at step 527. For example, when user wake-up is detected, the control device 240 may control brightness of at least one electronic device 250 to a maximum value for a predetermined time. This is to assist user waking after wake-up. Further, when user wake-up is detected, the control device 240 may control to output the first wavelength band of at least one electronic device 250 to be exaggerated more than a normal value for the predetermined time.

The control device 240 may determine at step 528 whether the predetermined time has elapsed. That is, when the predetermined time has elapsed, the control device 240 may determine whether a waking time has arrived.

If a waking time has arrived, the control device 240 may control to output brightness and a first wavelength band of at least one electronic device 250 that exaggerates the output of brightness and a wavelength to a normal state at step 529.

Figure 5C:
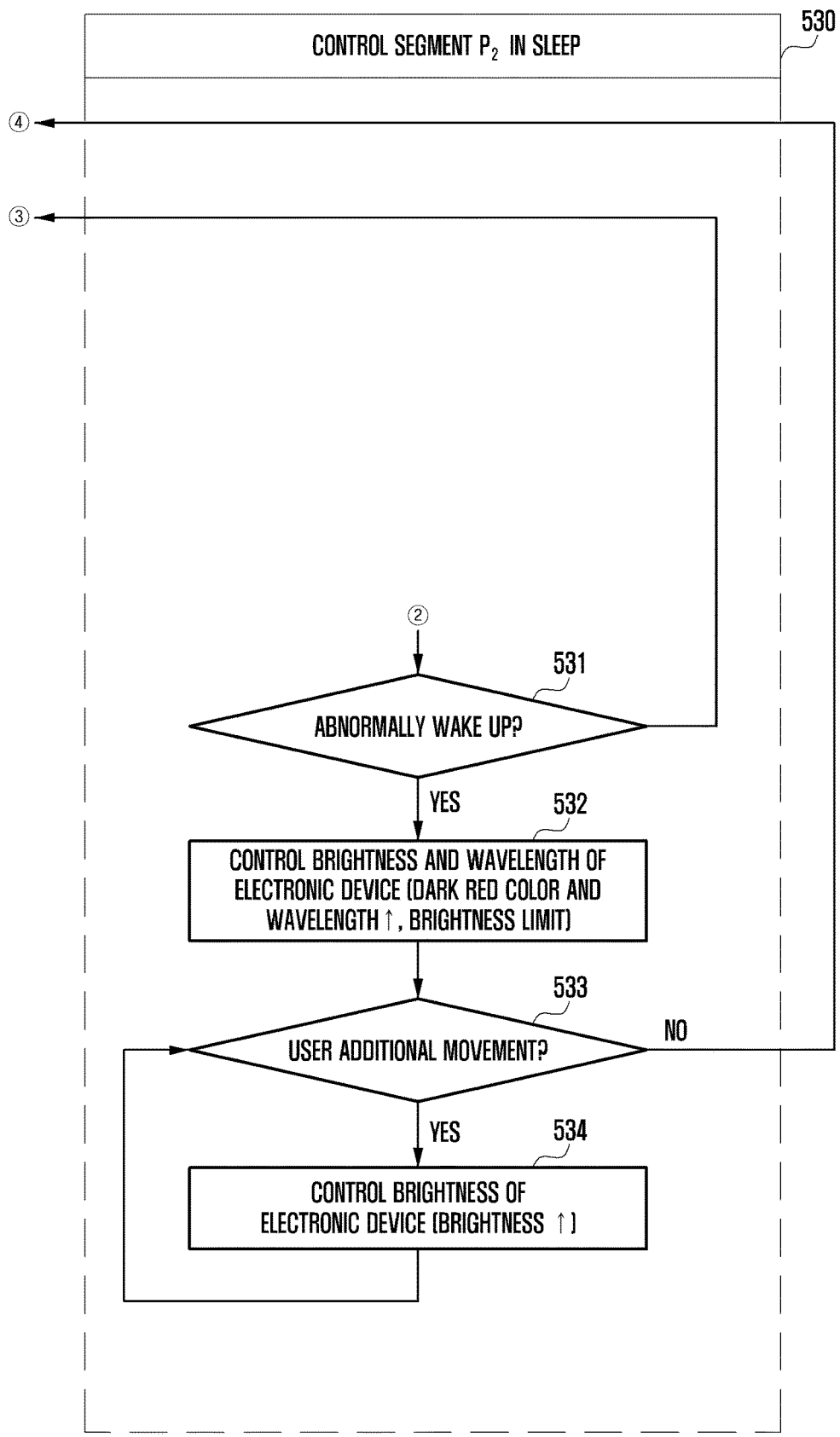
FIG. 5C is a flowchart illustrating a control method at a user sleep control segment according to a third exemplary embodiment of the present invention.

FIG. 5C is a flowchart illustrating a control method 530 of the smart home system 200 at a control segment $P_2$ in sleep.

As a determination result of the control device 240, the user may not enter a NREM sleep stage immediately before a wake-up time at step 524. In this case, the control device 240 may detect at step 531 whether the user abnormally wakes up. For example, at generally normal wake-up, because the user has not entered a deep sleep stage for approximately two hours before wake-up, a NREM sleep rate is high for a corresponding time. Therefore, the control device 240 may determine other wake-up to abnormal wake-up.

If the user abnormally wakes up, the control device 240 may control brightness and/or a wavelength of at least one electronic device 250 at step 532. For example, the control device 240 may increase slowly or at once brightness of the at least one electronic device 250 within a limited value (e.g., 10 lux). Further, the control device 240 may partially exaggerate a second wavelength band output and output a second wavelength band. The second wavelength band may include, for example, a dark red wavelength. Further, the control device 240 may partially block (remove) a first wavelength band (e.g., blue wavelength) output and output a first wavelength band (e.g., blue wavelength).

The control device 240 may detect at step 533 whether a user additional movement exists. If a user additional movement exists, the control device 240 may increase brightness of the at least one electronic device 250 step-by-step to the limited value or more at step 534.

When the user maintains an in-bed state and again sleeps, the system may again perform a control method 510 of the control segment $P_0$ while the user is in a bed.

FIG. 6 is a diagram illustrating an example of a method in which the signal processing unit 220 calculates sleep information with sensing data.

With reference to FIG. 6, for example, the signal processing unit 220 may primarily process the sensing data to generate meaningful data (e.g., breath, movement, heart rate variability, or heart rate) necessary for obtaining user sleep related information, as shown in 605. In this case, the signal processing unit 220 may search for a pattern of corresponding sensing data based on a data pattern defined at a database to detect breath, movement, heart rate variability, or heart rate. For example, when sensing data are an image input, the signal processing unit 220 may detect a user movement through a pixel movement with a previous frame. Further, the signal processing unit 220 may obtain information related to a user hypnagogic stage and sleep stage from the sensing data. The signal processing unit 220 may search for a corresponding sensing data pattern based on a data pattern defined at the database to detect a user sleep stage. Although a user sleep stage, movement, breath, heart rate variability, and heart rate each exist as an individual value, a mutual cause-and-effect relationship exists; thus, other data may be estimated from at least one of such data.

The signal processing unit 220 may secondarily process the primarily processed data, as shown in 610. The signal processing unit 220 may calculate a data change, a stabilizing speed, and/or a value range of the primarily processed data (e.g., breath, movement, heart rate variability, or heart rate).

For example, when input sensing data are d, a data change, a stabilizing speed, and/or a value range of primarily processed data may be obtained as follows.

Data change: $\Delta x$ (=xt−xt−1, the data change approaches 0 as a user closes to a sleep state.)

Stabilizing speed: $\int \Delta\Delta x \, dx$ ($\approx \Delta x$, the stabilizing speed approaches 0 as a user closes to a sleep state.)

Range of value: range of x (e.g., the breath number: 30)

The signal processing unit 220 may have a sleep data database at the inside or the outside, as shown in 615. The signal processing unit 220 may divide a sleep stage based on a previously defined value, and a threshold value may be determined by comparing sensing data, processed data, and a sleep stage (e.g., the breath number 30, $\Delta x=1$, $\int \Delta\Delta x \, dx=1$ when entering a NREM stage). Such data may be accumulated and stored at the database and be stored as a sleep pattern or a statistic value. The signal processing unit 220 analyzes a sleep pattern or statistics stored at the database, as shown in 620 to analyze a data change, stabilizing speed, and/or value range related to a movement, breath, heart rate variability, or heart rate from a user awake stage until entering a sleep stage.

The signal processing unit 220 matches data related to a data change, a stabilizing speed, and/or a value range related to a movement, breath, heart rate variability, or heart rate at a user awake stage, a hypnagogic stage, and a first NREM sleep stage stored at the database to a processed data, as shown in 625. In this case, the signal processing unit 220 may search for a close value of the processed data among statistic values stored at the database, determine the close value to a reference, and change and calculate a time domain at a time point in which a data change, a stabilizing speed, and a value range sequentially correspond with a determined reference value.

The signal processing unit 220 may calculate a user hypnagogic stage immersion level based on the matching, as shown in 630. For example, the signal processing unit 220 may determine or estimate the remaining time until entering a NREM stage with matched data and calculate a hypnagogic stage immersion level using an equation of current time—reference time/the remaining time until entering a NREM stage.

Figure 7:
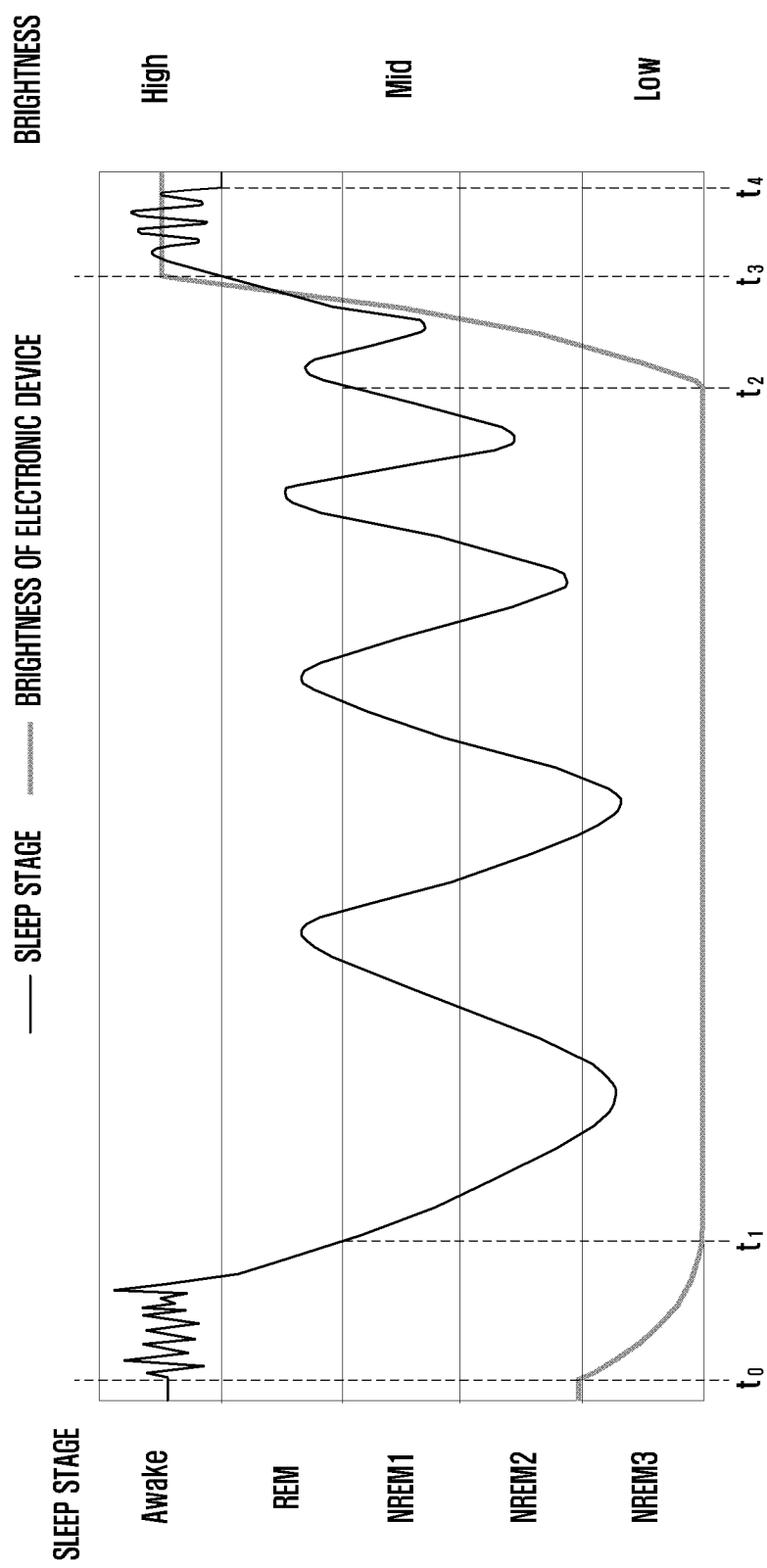
FIG. 7 is a graph illustrating a method of controlling brightness of an electronic device output for managing a user sleep environment according to a third exemplary embodiment of the present invention.

FIG. 7 is a graph illustrating a method in which the control device 240 controls brightness of at least one electronic device 250 at a hypnagogic stage control segment $P_0$ and a wake-up control segment $P_3$.

The control device 240 may slowly reduce brightness of the at least one electronic device 250 from a time point $t_0$ in which user hypnagogic stage preparation is detected. When entrance to a user first NREM sleep stage is detected, the control device 240 may turn off the at least one electronic device 250 or may turn off lighting and/or display of the at least one electronic device 250.

Thereafter, when it is detected that the user enters a REM sleep stage immediately before a wake-up time $t_3$, the control device 240 may control to have a maximum value at the wake-up time $t_3$ while slowly increasing brightness of the at least one electronic device 250 from a corresponding time $t_2$. While maintaining brightness of the at least one electronic device 250 at a maximum value for a predetermined time, the control device 240 may control brightness thereof to a normal value at a time point $t_4$ at which the predetermined time has elapsed.

FIG. 8 is a flowchart illustrating a method in which the control device 240 controls a blocking rate of a first wavelength band output of at least one electronic device 250 at a hypnagogic stage control segment $P_0$.

With reference to FIG. 8, the control device 240 may preset a maximum blocking rate of a first wavelength band output of at least one electronic device 250 at step 800. The maximum blocking rate may be set to correspond to a maximum blocking rate that a system may support. Thereafter, when a user is in a hypnagogic stage control segment, the control device 240 may determine a user hypnagogic stage immersion level at step 805. The control device 240 may increase the blocking rate based on the determined hypnagogic stage immersion level at step 810. The control device 240 may increase a blocking rate even without a change of a hypnagogic stage immersion rate.

The control device 240 may determine at step 815 whether the blocking rate is the predetermined maximum blocking rate. If the blocking rate is the predetermined maximum blocking rate, when the user enters a first NREM sleep stage without the additional control, the control device 240 may turn off the at least one electronic device 250 or may turn off lighting or display of the at least one electronic device 250.

If the blocking rate is not the predetermined maximum blocking rate, the control device 240 may detect at step 820 whether a user abnormal movement exists. If a user abnormal movement does not exist, the control device 240 may continue to increase a blocking rate. If a user abnormal movement is detected, the control device 240 may fix or reduce a blocking rate at step 825.

The control device 240 may accumulate and store at step 830 the user hypnagogic stage immersion level and a blocking rate corresponding thereto obtained at step 815 or step 825 at a database. The control device 240 may calculate data accumulated at the database with a blocking rate according to a sleep immersion rate in a user's next hypnagogic stage.

According to various exemplary embodiments, at least a portion of a method (e.g., operations) or a device (e.g., modules or functions thereof) according to the present disclosure may be implemented into an instruction stored at computer-readable storage media in a form of, for example, a programming module. When the instruction is executed by at least one processor (e.g., the processor), the at least one processor may perform a function corresponding to the instruction. The computer readable storage media may be, for example, the memory. At least a portion of the programming module may be implemented (e.g., executed) by, for example, the processor. At least a portion of the programming module may include, for example, a module, a program, a routine, sets of instructions, or a process for performing at least one function.

The computer-readable storage media may include magnetic media such as a hard disk, a floppy disk, and a magnetic tape; optical media such as a Compact Disc Read Only memory (CD-ROM) and a Digital Versatile Disc (DVD); magneto-optical media such as a floptical disk; and a hardware device, specially configured to store and perform a program command (e.g., a programming module), such as a Read Only memory (ROM), a Random Access memory (RAM), and a flash memory. Further, a program command may include a high-level language code that may be executed by a computer using an interpreter as well as a machine language code generated by a compiler. In order to perform an operation of the present disclosure, the above-described hardware device may be configured to operate as at least one software module and vice versa.

A module or a programming module according to the present disclosure may include at least one of the foregoing elements, may omit some elements, or may further include additional other elements. Operations performed by a module, a programming module, or another element according to the present disclosure may be executed with a sequential, parallel, repeated, or heuristic method. Further, some operations may be executed in different orders, may be omitted, or may add other operations.

Exemplary embodiments disclosed in this specification and drawings are suggested as a specific example to easily describe the present disclosure and to help understanding thereof and do not limit the scope of the present disclosure. Therefore, it should be understood that changes and variations obtained based on the spirit and scope of the present disclosure in addition to exemplary embodiments disclosed herein are included in the scope of the present disclosure.

The invention claimed is:

1. A method of controlling a control device for managing a user's sleep environment, the method comprising:
   obtaining sleep related information of the user based on user sensing data sensed by a sensor; and
   adjusting a first wavelength band output of at least one electronic device comprising a light source based on the sleep related information,
   wherein the step of adjusting a first wavelength band output of the at least one electronic device comprising a light source based on the sleep related information comprises:
      determining, based on the user sleep related state being a hypnagogic stage, the user hypnagogic stage immersion level to increase a blocking ratio of the first wavelength band output within a maximum blocking ratio; and fixing or reducing, based on a user abnormal movement being detected, the blocking ratio of the first wavelength band output, wherein the light source of the at least one electronic device is a display that simultaneously emits light of a plurality of wavelengths, the sleep related information comprises at least one of a user sleep related state and a user hypnagogic stage immersion level, wherein the sleep related information comprises the user hypnagogic stage immersion level, the user hypnagogic stage immersion level and the blocking ratio of the first wavelength band output corresponding thereto are accumulated in a database, and the blocking ratio of the first wavelength band output according to the user hypnagogic immersion level is calculated at a next hypnagogic stage based on the database, wherein the hypnagogic stage immersion level is determined by comparing at least one of a data change, a data stabilizing speed, or a data value range of obtained data with a reference value stored in a database, and wherein the hypnagogic immersion level represents an immersion execution rate until the user enters a non-rapid-eye movement stage when the user sleeps.

2. The method of claim 1, further comprising determining the user hypnagogic stage immersion level to reduce brightness of the light source, based on the user sleep related state is a hypnagogic stage.

3. The method of claim 1, further comprising:
detecting, based on the user sleep related state is a sleep stage, the user abnormal wake-up based on a predetermined wake-up time or a user sleep pattern;
increasing, based on the abnormal wake-up is detected, the light source within limited brightness;
controlling to perform, based on the abnormal wake-up is detected, at least one of partial blocking of the first wavelength band output and partial exaggeration of a second wavelength band output; and
increasing, based on a user additional movement is detected, brightness of the light source further than the limited brightness.

4. The method of claim 1, wherein obtaining sleep related information of a user based on user sensing data sensed by a sensor comprises:
determining whether a user enters a rapid-eye movement (REM) state immediately before wake-up based on a predetermined wake-up time or a user sleep pattern,
wherein the method further comprises increasing brightness of the light source, based on a user enters an REM state, and
wherein adjusting a first wavelength band output of at least one electronic device comprising a light source based on the sleep related information comprises controlling to partially exaggerate, based on user wake-up is detected, the first wavelength band output for a predetermined time.

5. The method of claim 1, wherein obtaining sleep related information of a user based on user sensing data sensed by a sensor comprises comparing at least one of a data change, stabilizing speed, and data value range of at least one of breath, movement, heart rate variability, and heart rate obtained from the sensing data with a reference value stored at a database based on the user sleep related state to calculate the user hypnagogic stage immersion level.

6. A control device for managing a user's sleep environment, the control device comprising:
a controller configured to obtain the user's sleep related information based on user sensing data sensed by a sensor and to generate a control signal that adjusts a first wavelength band output of at least one electronic device comprising a light source based on the sleep related information;
a memory configured to store a database; and
a transceiver configured to transmit the control signal to the at least one electronic device,
wherein the light source of the at least one electronic device is a display that simultaneously emits light of a plurality of wavelengths, and the sleep related information comprises at least one of a user sleep related state and a user hypnagogic stage immersion level,
wherein the sleep related information comprises the user hypnagogic state immersion level, the controller is configured to determine the user hypnagogic stage immersion level to generate a control signal that increases a blocking ratio of the first wavelength band output within a maximum blocking ratio based on the user sleep related state is a hypnagogic stage, to generate a control signal that fixes or reduces the blocking ratio of the first wavelength band output based on a user abnormal movement is detected, to accumulate the user hypnagogic stage immersion level and the blocking ratio of the first wavelength band output corresponding thereto at the database, and to calculate the blocking ratio of the first wavelength band output according to the user hypnagogic stage immersion level at a next hypnagogic stage based on the database,
wherein the hypnagogic stage immersion level is determined by comparing at least one of a data change, a data stabilizing speed, or a data value range of obtained data with a reference value stored in the database, and
wherein the hypnagogic immersion level represents an immersion execution rate until the user enters a non-rapid-eye movement stage when the user sleeps.

7. The control device of claim 6, wherein the controller is configured to determine the user hypnagogic stage immersion level to reduce brightness of the light source, based on the user sleep related state is a hypnagogic stage.

8. The control device of claim 6, wherein the controller is configured to detect user abnormal wake-up based on a predetermined wake-up time or a user sleep pattern based on the user sleep related state is a sleep stage, to generate a control signal that increases brightness of the light source within limited brightness based on the abnormal wake-up is detected, to generate a control signal that performs at least one of first wavelength band output partial blocking and second wavelength band output partial exaggeration based on the abnormal wake-up is detected, and to generate a control signal that increases brightness of the light source further than the limited brightness based on a user additional movement is detected.

9. The control device of claim 6, wherein the controller is configured to determine whether a user enters an REM state immediately before wake-up based on a predetermined wake-up time or a user sleep pattern and to generate a control signal that increases brightness of the light source, based on a user enters an REM state.

10. The control device of claim 9, wherein the controller is configured to generate a control signal that controls to partially exaggerate the first wavelength band output for a predetermined time, based on user wake-up is detected.

11. The control device of claim 6, further comprising a memory configured to store a database,
   wherein the controller is configured to compare at least one of a data change, a stabilizing speed, and a data value range of at least one of breath, movement, heart rate variability, and heart rate obtained from the sensing data with a reference value stored at a database based on the user sleep related state to calculate the user hypnagogic stage immersion level.

\* \* \* \* \*